United States Patent [19]

Crabb et al.

[11] 4,407,670
[45] Oct. 4, 1983

[54] BIOCIDAL COMPOUNDS AND COMPOSITIONS

[75] Inventors: Trevor A. Crabb; Graham C. Jackson, both of Portsmouth; Philip A. Jupp, Petersfield, all of England

[73] Assignee: National Research Development Corporation, London, England

[21] Appl. No.: 237,108

[22] Filed: Feb. 23, 1981

[30] Foreign Application Priority Data

Feb. 28, 1980 [GB] United Kingdom ................ 8006772

[51] Int. Cl.$^3$ .................... A01N 43/00; A01N 43/40; A01N 43/76
[52] U.S. Cl. ........................................ 71/67; 71/88; 71/94; 44/63; 424/267; 424/272; 106/16; 106/18.32; 546/112; 546/240
[58] Field of Search ............... 71/66, 67, 94; 546/240, 546/115, 112; 424/256, 267, 272

[56] References Cited

U.S. PATENT DOCUMENTS

| | | | |
|---|---|---|---|
| 3,375,249 | 3/1968 | Johnson | 546/115 |
| 3,560,511 | 2/1971 | Bernardi et al. | 546/240 |
| 3,854,926 | 12/1974 | Senkbeil | 71/94 |
| 3,906,098 | 9/1975 | Barlow et al. | 71/67 |
| 4,074,999 | 2/1978 | Quinlan | 71/67 |
| 4,304,894 | 12/1981 | Andrews et al. | 71/67 |

FOREIGN PATENT DOCUMENTS 227422 2/1959 Australia ............................. 546/240

OTHER PUBLICATIONS

Tilford et al., "Diuretics αα-Disubstituted, etc.", (1954), JACS 76, pp. 2431-2441, (1954).
Crabb et al. I, "Configurational, etc.", (1968), Tetrahedron, 24, pp. 1997-2011, (1968).
Crabb et al. II, "Stereochemical Studies, etc.", (1966), J. Hetero. Chem. 3, pp. 418-421, (1966).

Arya et al., "Synthesis of New Heterocycles, etc.", (1976), CA87, No. 5882v, (1977).

Primary Examiner—Glennon H. Hollrah
Attorney, Agent, or Firm—Cushman, Darby & Cushman

[57] ABSTRACT

Biocidal compositions and methods of inhibiting biological growth employ, as the active agent, certain monocyclic and bicyclic heterocyclic compounds, some novel perse, of general formula I

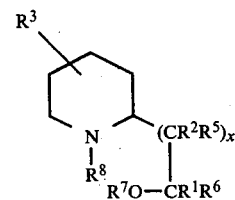

in which X is 0,1 or 2, $R^1$, $R^2$, $R^5$ and $R^6$ are a hydrogen atom, an alkyl radical containing up to 20 carbon atoms or an aryl radical; $R^3$ is a hydrogen atom or a lower alkyl radical containing up to 6 carbon atoms; and $R^7$ and $R^8$, when taken separately, are hydrogen atoms or, when taken together, are

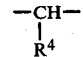

in which $R^4$ is a hydrogen atom, an alkyl radical containing up to 16 carbon atoms or an aryl radical.

The preferred active agents generally have low solubility in sea water, are toxic to algal, barnacle or fungal growth, and are colorless. They may be used to form anti-fouling paints free from undesirable heavy metals or as anti-fungal additives in hydrocarbon fuels.

5 Claims, No Drawings

BIOCIDAL COMPOUNDS AND COMPOSITIONS

The invention relates to the use of certain nitrogen and oxygen containing heterocyclic compounds as biocidal agents to novel biocidal compositions, for use in marine and fresh-water environments, which contain said novel biocidal agents and to certain novel heterocyclic organic compounds suitable for such use.

The term "biocidal" as used herein relates to the prevention of undesirable biological growth, for example, algal, barnacle or fungal growth on submerged, partially submerged or damp exposed structures in aquatic environments or fungal growth in hydrocarbon fuels.

All underwater surfaces are liable to become covered by algal and barnacle growth which can lead to damage to paintwork and structure. On moving vessels such growth also produces resistance to movement increasing fuel costs etc. Whilst all surfaces are likely to become coated, comparatively stationary structures such as jetties, piers and ships ridings at anchor are most severely affected. Such growth can be inhibited by so-called anti-fouling paints applied at regular intervals. The active ingredients of said paints are frequently also effective in preventing fouling of submerged and exposed structures by fungal growth. However, commonly used biocidal agents, normally metal salts or organometallic compounds, have a relatively short effective life, eg cuprous salts, and/or are toxic to desirable marine organisms and often to man, eg lead and mercury salts, and/or because of their generally coloured nature substantially restrict the colour change of compositions containing them.

It has now been found that certain heterocyclic compounds containing a piperidyl ring system possess algicidal and barnicidal activity at low concentrations whilst generally having low sea water solubility thus increasing useful life and reducing toxic effects away from the treated surface. Further the biocidal agents of this invention are relatively simple and inexpensive to prepare and do not, because of their generally colourless nature, substantially restrict the colour range of compositions containing them.

According to the present invention there is provided a biocidal composition comprising an active concentration of an active component which is at least one heterocyclic compound of general formula I

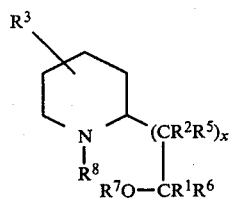

wherein
X is 0, 1 or 2;
$R^1$, $R^2$, $R^5$ and $R^6$ are the same or different and each is a hydrogen atom, an alkyl radical containing up to 20 carbon atoms or an aryl radical;
$R^3$ is a hydrogen atom or a lower alkyl radical containing up to 6 carbon atoms; and
$R^7$ and $R^8$, when taken separately, are hydrogen atoms or, when taken together, are

wherein $R^4$ is a hydrogen atom, an alkyl radical containing up to 16 carbon atoms or an aryl radical; in conjunction with an acceptable diluent or carrier.

Preferably the at least one heterocyclic compound has general formula II

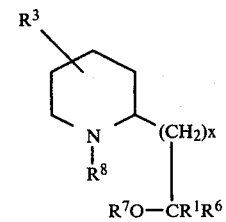

wherein X, $R^1$, $R^2$, $R^4$, $R^6$, $R^7$ and $R^8$ are as defined above. Particularly preferred biocidal compositions according to the present invention have the following heterocyclic compounds as active components, for example compounds of general formula II wherein X is 0, 1 or 2; $R^1$ is an alkyl radical containing from 8 to 12 carbon atoms; $R^3$ and $R^6$ each is a hydrogen atom; and $R^7$ and $R^8$,
when taken separately, are hydrogen atoms or, when taken together, are —$CH_2$—
especially compounds wherein
X is 0; $R^1$ is n—$C_{10}H_{21}$; $R^3$ and $R^6$ each is a hydrogen atom; and $R^7$ and $R^8$, when taken separately, are hydrogen atoms, or, when taken together, are —$CH_2$—;
and wherein
X is 2; $R^1$ is n—$C_8H_{17}$; $R^3$ and $R^6$ each is a hydrogen atom; and $R^7$ and
$R^8$, when taken separately, are hydrogen atoms or, when taken together, are —$CH_2$—;
or compounds of general formula II wherein X is 0, 1 or 2; $R^1$ and $R^6$ are the same or different and each is a hydrogen atom or a methyl radical; $R^3$ is a hydrogen atom, a methyl radical or an ethyl radical; and $R^7$ and $R^8$, when taken separately, are hydrogen atoms or, when taken together, are

wherein $R^4$ is an alkyl radical containing up to 12 carbon atoms or an aryl radical substituted by at least one electron withdrawing substituent group; more particularly compounds wherein X is 0, 1 or 2; $R^1$ and $R^6$ each is a hydrogen atom; $R^3$ is a hydrogen atom; a methyl radical or an ethyl radical; $R^7$ and $R^8$, when taken separately, are hydrogen atoms or, when taken together, are —CH$R^4$— wherein $R^4$ is an alkyl radical containing from 7 to 12 carbon atoms or an aryl radical substituted by at least one electron withdrawing substituent group;
especially compounds wherein;

X is 0, 1 or 2; $R^1$, $R^3$ and $R^6$ each is a hydrogen atom; and $R^7$ and $R^8$ are taken together and are p-$O_2NC_6H_5CH$; and wherein;

X is 0, 1 or 2; $R^1$ and $R^6$ each is a hydrogen atom; $R^3$ is an ethyl radical; and $R^7$ and $R^8$ are taken separately and are hydrogen atoms.

The acceptable diluent or carrier may be any of the diluents or carriers that are conventially used in biocidal compositions. For example vinyl, resin, epoxy or mixed media, and a suitable solvent medium may be used. The proportion of biocidal agent used in the compositions of the present invention will vary with the carrier and active component used, but will normally be within the range 10% to 50% by weight of the dry paint film. Significantly, compositions containing an active component of this invention and a rosin carrier do not exhibit the well known phenomenom of "drying out" shown by copper containing rosins (ie compositions in which a copper compound is the toxicant and a rosin is the carrier). Further the range of colours of compositions containing active components of this invention is far wider than that which can be obtained from conventional copper based compositions. In particular a black biocidal composition is produced by mixing a suitable carrier and solvent with an active component according to this invention and carbon black.

One of the most preferred active components in this black composition is 1-n-decyl perhydro oxazolo (3, 4-a) pyridine.

The active components of the present invention may also be used, with or without a diluent or carrier, as additives to fuels, in particular hydrocarbon fuels, in order to stop or significantly inhibit the growth of fungus in or on the fuel. Active components that are particularly useful as anti-fungicides are 1-n-alkyl-2-piperidyl carbinols and 1-n-alkyl perhydro oxazolo (3, 4-a) pyridines; wherein, in both cases, the 1-n-alkyl radical contains from 8 to 12 carbon atoms inclusive.

The active components according to this invention exhibit varying degees of algicidal and barnicidal toxicity. The degree of toxicity of said components appears to be determined at least in part by the size of the radical $R^1$, $R^2$, $R^3$, $R^4$, $R^5$ and $R^6$. In particular active components of general formula II in which X is 0, $R^1$ is an alkyl radical containing from 8 to 12 carbon atoms inclusive; $R^3$ and $R^6$ each is a hydrogen atom and $R^7$ and $R^8$, when taken separately, are hydrogen atoms or, when taken together, are —$CH_2$— have been found to possess particularly good algicidal and barnicidal properties.

One of the most preferred active components according to this invention is 1-n-decyl perhydro oxazolo (3, 4-a) pyridine.

Active components according to this invention that are particularly effective as anti-fouling agents have a low degree of solubility in water. In general an active component of general formula I, wherein $R^7$ and $R^8$ are taken separately and are hydrogen atoms, will be more soluble in water than an active component of general formula I, wherein $R^7$ and $R^8$ are taken together and are —$CHR^4$—, of comparable molecular weight. Further active components of general formula I which contain higher alkyl radicals are generally less soluble in water than those which contain lower alkyl radicals.

The present invention further provides a method of inhibiting undesirable biological growth in aquatic or hydrocarbon environments comprising applying a biocidal composition according to the present invention to prevent biological growth.

A biocidal composition, in the form of a paint, may be coated onto any surface that is in an aquatic, especially a marine, environment. In particular, structures such as jetties, piers and ships either riding at anchor or in motion may be protected against biological growth by the method and composition of the present invention.

Additionally, a biocidal composition according to the present invention may be used in the method of this invention to prevent fungal growth in hydrocarbon fuels.

The present invention further provides novel heterocyclic compounds which may be used as active components in the biocidal compositions of the present invention.

These novel heterocyclic compounds have the general formula I or II above wherein X is 0 or 1; $R^1$ is an alkyl radical containing from 5 to 20 carbon atoms or an aryl radical substituted by at least one electron withdrawing substiteunt group; $R^2$, $R^5$ and $R^6$ are the same or different and each is a hydrogen atom, an alkyl radical containing up to 20 carbon atoms or an aryl radical substituted by at least one electron withdrawing substituent group; $R^3$ is a hydrogen atom or a lower alkyl radical containing up to 6 carbon atoms; and $R^7$ and $R^8$, when taken separately, are hydrogen atoms or, when taken together, are

wherein $R^4$ is a hydrogen atom, an alkyl radical containing up to 16 carbon atoms or an aryl radical substituted by at least one electron withdrawing substituent group; especially wherein X is 0, $R^1$ is an alkyl radical containing from 8 to 12 carbon atoms, particularly n—$C_{10}H_{21}$; $R^2$, $R^3$, $R^5$ and $R^6$ each is a hydrogen atom; and $R^7$ and $R^8$, when taken separately, are hydrogen atoms or, when taken together, are —$CH_2$—; and also have the general formula I or II above wherein X is 2; $R^1$, $R^2$, $R^5$ and $R^6$ are the same or different and each is a hydrogen atom, an alkyl radical containing up to 20 carbon atoms or an aryl radical; $R^3$ is a hydrogen atom or a lower alkyl radical containing up to 6 carbon atoms; and $R^7$ and $R^8$, when taken separately, are hydrogen atoms or, when taken together, are

wherein $R^4$ is hydrogen atom, an alkyl radical containing up to 16 carbon atoms or an aryl radical; especially wherein X is 2; at least one of the groups $R^1$, $R^3$ and $R^4$ is a methyl radical, an ethyl radical, an alkyl radical containing from 7 to 12 carbon atoms or an aryl radical substituted by at least one electron withdrawing substituent, $R^2$, $R^5$ and $R^6$ each is a hydrogen atom; and $R^7$ and $R^8$, when taken separately, are hydrogen atoms or, when taken together, are —$CH_2$—;

most especially wherein

X is 2, $R^1$ is n—$C_8H_{17}$; $R^1$, $R^3$, $R^5$ and $R^6$ each is a hydrogen atom; and $R^7$ and $R^8$, when taken separately, are hydrogen atoms or, when taken together, are —CH$_2$—; but excluding heterocyclic compounds of general formula I wherein
X is 2, R$^1$, R$^2$, R$^5$ and R$^6$ each is a hydrogen atom; R$^3$ is a hydrogen atom, a methyl radical or an ethyl radical; and R$^7$ and R$^8$, when taken separately, are hydrogen atoms or, when taken together, are —CH$_2$—;

The active components of the biocidal compositions of the present invention may be prepared by various methods depending on the value of X, on the nature of the alkyl radicals R$^1$, R$^2$, R$^3$, R$^4$, R$^5$ and R$^6$, and on the starting materials available.

For example, a particularly favourable route to 2-piperidyl carbinols which uses cheap starting materials and gives high yields for all steps is illustrated in Scheme I Scheme I

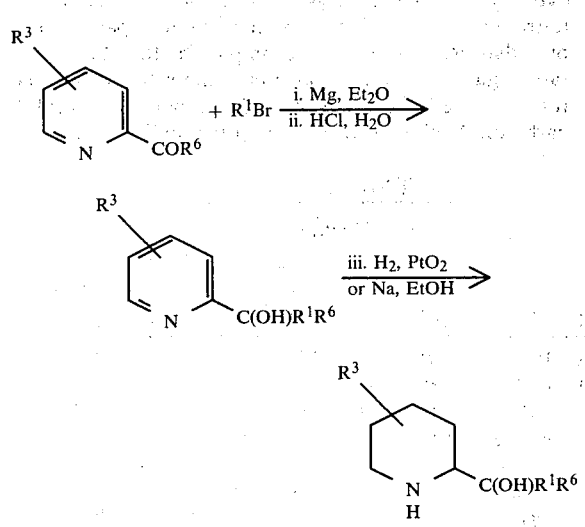

Similarly 2-(α-piperidyl) ethanols may be prepared from fairly cheap starting materials and in high yield by the method of Scheme II, Scheme II

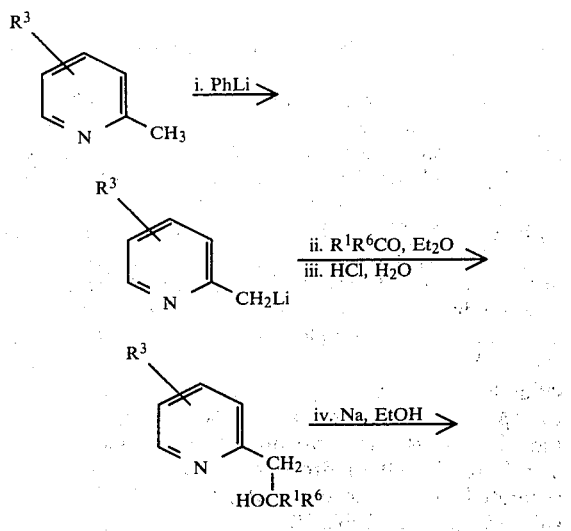

Scheme II
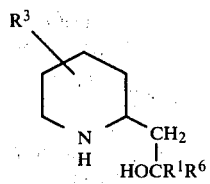

Finally perhydro oxazolo (3, 4-a) pyridines or perhydro pyrido (1, 2-c) (1, 3) oxazines may be readily prepared from the above piperidyl alcohols by reaction with an aqueous solution of an alkyl aldehyde, especially formal dehyde. A typical reaction is shown in Scheme III.

Scheme III

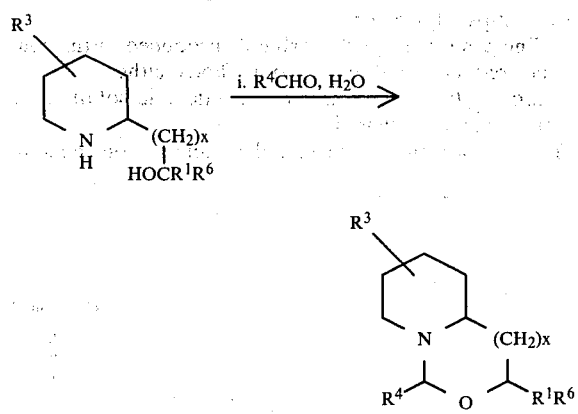

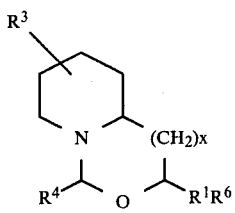

The conversion of a 2-piperidyl carbinol into a perhydro oxazolo (3, 4-a) pyridine as described above has been reported previously by T. A. Crabb and R. F. Newton, J Heterocycl. Chem., 1966, 3, 418.

All of the active components produced by the above processes are mixtures of diastereoisomers. In some cases the diastereoisomeric mixture could be separated by fractional crystallisation or column chromatography. For example, fractional crystallisation gave two pure diastereoisomers from the mixtures of each of α-ethyl, α-n-pentyl and α-n-octyl-2-piperidylcarbinol whilst column chromatography separated the diastereoisomeric mixtures of 1-methyl, 1-n-octyl and 1-n-dodecyl perhydro oxazolo (3, 4-a) pyridine. However, in all the tests performed on the above components of this invention to ascertain their anti-fouling and anti-fungal activities, the diastereoisomeric mixture of the agent, rather than one of its pure diastereoisomers, was employed, although the activity may, in fact, be associated with only one of the isomers.

The relatively simple and inexpensive preparation of active components in accordance with the formulae I and II, as defined herein, represents the major advantage of these active components over previously disclosed (UK patent appln. No. 19035/75) organic active components containing a piperidyl ring.

Biocidal compositions, methods of inhibiting biological growth, novel heterocyclic compounds and methods of preparation of active components according to the present invention will now be described by way of example only.

EXAMPLES 1 TO 9

Preparation of certain-2-piperidyl carbinols.

A solution of the appropriate alkyl bromide (1 Mole) in sodium dried ether (450 ml) was added dropwise with stirring to dry magnesium turnings (24 g) over a period of 0.75h.

When the reaction was completed, the flask was cooled in ice and a solution of 2-pyridine aldehyde (1.0 Mole, 107 g) in sodium dried ether (220 ml) was added carefully over 1h. The reaction mixture was then heated under reflux for 0.5h on a water bath. Dilute hydrochloric acid (700 ml., 1.5 N) was then added and this was followed by the addition of enough aqueous sodium carbonate to basify the mixture. The aqueous layer was separated from the organic layer and then extracted with ether (3×500 ml). The combined ether extracts were dried ($Na_2SO_4$) and evaporated in vacuo to give a brown residue. This brown residue was then purified by distillation under reduced pressure to afford an α-alkyl-2-pyridylcarbinol.

The α-alkyl-2-pyridylcarbinols produced in this way were reduced by one of two methods, either
  i. catalytic hydrogenation in acetic acid solution, or
  ii. sodium in ethanol.

The method chosen depended principally on the solubility of the α-alkyl-2-pyridylcarbinol in acetic acid or ethanol. For example, α-n-decyl, α-n-dodecyl, and α-n-hexadecyl-2-pyridylcarbinol were only slightly soluble in glacial acetic acid, and therefore the reduction of these compounds was effected by the sodium in ethanol method.

i. Catalytic hydrogenation

α-Alkyl-2-pyridylcarbinol (0.3 Mole) was dissolved in glacial acetic acid (180 ml) containing Adams platinum oxide catalyst (1 g) and reduced by hydrogen at 60 lbs in $^{-2}$ in a Parr hydrogenator. When the reduction was completed, the catalyst was filtered off, the acetic acid was removed in vacuo and the residue was basified with 50% aqueous sodium hydroxide. This solution was then extracted with ether (3×200 ml), the combined extracts dried ($Na_2SO_4$) and concentrated to yield α-alkyl-2-piperidylcarbinol as a crystalline mixture of diastereoisomers.

ii. Sodium in ethanol

A solution of the α-alkyl-2-pyridylcarbinol (0.25 Mole) in absolute ethanol (650 ml) was boiled under reflux whilst sodium metal (75 g) was added portionwise over a period of approximately 0.75h. When the addition was completed the solution was refluxed for a further 2 hr and then cooled (to ambient temperature) and carefully acidified (to pH 1) by the addition of, consecutively, dilute hydrochloric acid (50 ml) and concentrated hydrochloric acid. The solution was basified with 30% aqueous sodium hydroxide and then extracted with ether. The combined ether extracts were dried ($Na_2SO_4$) and evaporated in vacuo to afford a dark brown residue of crude α-alkyl-2-piperidylcarbinol. The α-2-piperidylcarbinol could be purified by crystallisation from an appropriate solvent eg petroleum ether.

In all cases the α-alkyl-2-piperidylcarbinol produced by either of these methods of reduction was a mixture of diastereoisomers. This diastereoisomeric mixture was employed in the biocidal tests described later. However, by fractional re-crystallisation or column chromatography over alumina it was possible to separate some pure diastereoisomers. For example, fractional crystallisation gave two pure diastereoisomers from the mixtures of α-ethyl,α-n-pentyl and α-n-octyl-2-piperidylcarbinol. Analytical results are given in Table I.

TABLE I 2-piperidylcarbinols

| Compound No | X | $R^1$ | $R^3$ | $R^6$ | Calculated (%) C | H | N | Found (%) C | H | N |
|---|---|---|---|---|---|---|---|---|---|---|
| 1 | O | H | $C_2H_5^a$ | H | 67.1 | 12.0 | 9.8 | 67.2 | 12.15 | 9.6 |
| 2 | O | $C_2H_5$ | $CH_3^b$ | H | 68.7 | 12.2 | 8.9 | 68.9 | 12.3 | 9.0 |
| 3 | O | n-$C_8H_{17}$ | H | H | 73.95 | 12.8 | 6.2 | 73.8 | 12.75 | 6.5 |
| 4 | O | n-$C_8H_{17}$ | $CH_3^b$ | H | 74.6 | 12.9 | 5.8 | 74.6 | 12.8 | 5.7 |
| 5 | O | n-$C_9H_{19}$ | H | H | 74.6 | 12.9 | 5.8 | 74.6 | 12.75 | 5.85 |
| 6 | O | n-$C_{10}H_{21}$ | H | H | 75.2 | 13.0 | 5.5 | 75.45 | 13.3 | 5.6 |
| 7 | O | n-$C_{11}H_{23}$ | H | H | 75.8 | 13.1 | 5.2 | 75.9 | 13.0 | 5.0 |
| 8 | O | n-$C_{12}H_{25}$ | H | H | 76.25 | 13.15 | 5.0 | 76.4 | 13.2 | 5.3 |
| 9 | O | n-$C_{16}H_{33}$ | H | H | 77.8 | 13.35 | 4.1 | 77.6 | 13.35 | 4.15 |

Note:
$^a$5-ethyl substituent;
$^b$6-methyl substituent;

EXAMPLES 10 TO 24c

Preparation of certain perhydro-oxazolo[3,4-a]pyridines.

A crude, non-recrystallised diastereoisomaric 2-piperidylcarbinol (0.2 Mole, prepared by one of the above methods) was shaken with an excess of an aqueous alkylaldehyde for 0.5h. The mixture was basified with 50% aqueous sodium hydroxide and extracted with ether (4×50 ml). The ethereal extracts were combined, dried ($Na_2SO_4$), evaporated and the residual oil distilled in vacuo to give a diastereoisomeric mixture of a perhydrooxazolo[3,4-a]pyridine. This diastereoisomeric mixture was employed in the biocidal tests described later. However, by fractional crystallisation or column chromatography over alumina it was possible to separate some pure diastereoisomers. For example the diastereoisomeric mixtures of 1-methyl, 1-n-octyl and 1-n-dodecylperhydro oxazolo[3,4-a]pyridine were separated by column chromatography. Analytical results are given in Table II.

TABLE II

Perhydro-oxazolo-(3,4-a)-pyridines

| Compound No | X | $R^1$ | $R^3$ | $R^4$ | $R^6$ | Calculated (%) C | H | N | Found (%) C | H | N |
|---|---|---|---|---|---|---|---|---|---|---|---|
| 10 | 0 | H | H | H | H | 66.1 | 10.3 | 11.0 | 66.4 | 10.45 | 11.0 |
| 11 | 0 | H | $CH_3^a$ | H | H | 68.05 | 10.7 | 10.0 | 68.1 | 10.6 | 10.1 |
| 12 | 0 | H | $C_2H_5^b$ | H | H | 69.6 | 11.0 | 9.0 | 69.6 | 11.05 | 8.9 |
| 13 | 0 | H | H | $C_2H_5$ | H | 69.6 | 11.0 | 9.0 | 69.65 | 11.2 | 9.1 |
| 14 | 0 | H | H | $n-C_7H_{15}$ | H | 74.6 | 12.1 | 6.2 | 74.5 | 12.1 | 6.3 |
| 15 | 0 | H | H | $n-C_{11}H_{23}$ | H | 76.8 | 12.5 | 5.0 | 76.7 | 12.3 | 5.15 |
| 16 | 0 | $C_2H_5$ | H | H | H | 69.6 | 11.05 | 9.0 | 69.6 | 11.0 | 8.8 |
| 17 | 0 | $nC_5H_{11}$ | H | H | H | 73.0 | 11.75 | 7.1 | 72.9 | 11.75 | 7.3 |
| 18 | 0 | $n-C_8H_{17}$ | H | H | H | 75.25 | 12.2 | 5.85 | 75.35 | 12.2 | 5.8 |
| 19 | 0 | $n-C_8H_{17}$ | $CH_3^a$ | H | H | 75.8 | 12.3 | 5.5 | 75.65 | 12.4 | 5.6 |
| 20 | 0 | $n-C_9H_{19}$ | H | H | H | 75.8 | 12.3 | 5.5 | 75.7 | 12.45 | 5.6 |
| 21 | 0 | $n-C_{10}H_{21}$ | H | H | H | 76.3 | 12.45 | 5.25 | 76.2 | 12.55 | 5.3 |
| 22 | 0 | $n-C_{11}H_{23}$ | H | H | H | 76.8 | 12.5 | 5.0 | 76.6 | 12.5 | 4.9 |
| 23 | 0 | $n-C_{12}H_{25}$ | H | H | H | 77.2 | 12.6 | 4.75 | 77.2 | 12.3 | 4.75 |
| 24 | 0 | $n-C_{16}H_{33}$ | H | H | H | 78.55 | 12.9 | 4.0 | 78.3 | 13.2 | 3.7 |
| 24a | 0 | $C_6H_5$ | H | $CH_3$ | H | 77.4 | 8.8 | 6.45 | 77.4 | 8.8 | 6.6 |
| 24b | 0 | $C_6H_5$ | H | H | $C_6H_5$ | 81.7 | 7.6 | 5.0 | 81.7 | 7.5 | 5.05 |
| 24c | 0 | $CH_3$ | H | $p-O_2NC_6H_5$ | H | | | | | | |

Note:
[a] 5-Methyl substituent;
[b] 6-Ethyl substituent

EXAMPLES 25 TO 28

Preparation of certain 2-(α-piperidyl)ethanols

Phenyl lithium was prepared by the reaction of freshly cut lithium metal (1 Mole, 7 g) in sodium dried ether (750 ml) with freshly distilled bromobenzene (0.5 Mole, 78.5 g) under an atmosphere of nitrogen. To this solution was added dropwise 2-methylpyridine (0.5 Mole, 46.5 g) in sodium dried ether (100 ml) and the resultant red/brown solution was stirred at room temperature for 1h. The reaction mixture was cooled in ice and a solution of n-alkyl aldehyde (0.5 Mole) in sodium dried ether (100 ml) was added slowly with stirring over a period of 0.5h. The reaction mixture was stirred for a further 1.5h after which time the pale yellow solution was acidified with 50% hydrochloric acid and stirred for 0.5h. The aqueous layer was separated, basified with a saturated aqueous solution of sodium carbonate and extracted with chloroform (4×100 ml). The combined extracts were dried ($K_2CO_3$), evaporated and the residue distilled in vacuo to yield 2-(α-pyridyl)-1-alkylethanol as a yellow oil or a low melting solid.

A solution of the 2-(α-pyridyl)-1-alkyl ethanol (0.25 Mole) in absolute ethanol (650 ml) was boiled under reflux whilst sodium metal (75 g) was added portionwise over a period of approximately 0.75h. The refluxing was continued for a further 2h, and then the solution was allowed to cool to ambient temperature. The cooled solution was carefully acidified (to pH 1) by the addition of, consecutively, dilute hydrochloric acid (50 ml) and concentrated hydrochloric acid. The solution was basified with 30% aqueous sodium hydroxide and ether extracted. The combined ether extracts were dried ($Na_2SO_4$), concentrated and the residue distilled in vacuo to give 2-(α-piperidyl)-1-alkyl ethanol. The diastereoisomeric mixture obtained was used in the biocidal tests given later. Analytical results are given in Table III.

TABLE III

2-(α-Piperidyl) ethanols.

| Compound No | X | $R^1$ | $R^2$ | $R^3$ | $R^5$ | $R^6$ | Calculated (%) C | H | N | Found (%) C | H | N |
|---|---|---|---|---|---|---|---|---|---|---|---|---|
| 25 | 1 | H | H | $C_2H_5^a$ | H | H | 68.75 | 12.2 | 8.9 | 68.6 | 12.2 | 8.85 |
| 26 | 1 | $C_2H_5$ | H | H | H | H | 68.75 | 12.2 | 8.9 | 68.9 | 12.1 | 8.7 |
| 27 | 1 | $n-C_7H_{15}$ | H | H | H | H | 74.0 | 12.9 | 6.2 | 74.2 | 13.0 | 6.15 |
| 28 | 1 | $n-C_{11}H_{23}$ | H | H | H | H | 76.3 | 13.15 | 4.9 | 76.3 | 13.0 | 5.15 |

Note:
[a] 5-ethyl substituent

EXAMPLES 29 TO 35

Preparation of certain perhydropyrido[-1,2-c][1,3]oxazines.

A 2-(α-piperidyl) ethanol (0.08 Mole, prepared as described above) was shaken with an excess of aqueous-alkyl aldehyde for 0.5h. The mixture was basified with 50% aqueous sodium hydroxide and extracted with ether. The ethereal extracts were combined, dried ($Na_2SO_4$), concentrated and the residual oil distilled in vacuo to give a diastereoisomeric mixture of a 1-alkyl-perhydro pyrido[1,2-c][1,3]oxazine. The diastereoisomer mixture obtained was used in the biocidal tests given later. Analytical results are given in Table IV.

TABLE IV

Perhydropyrido [1,2-c] [1,3] oxazines

| Compound No | X | R¹ | R² | R³ | R⁴ | R⁵ | R⁶ | Calculated (%) C | H | N | Found (%) C | H | N |
|---|---|---|---|---|---|---|---|---|---|---|---|---|---|
| 29 | 1 | H | H | H | H | H | H | 68.05 | 10.7 | 9.9 | 68.1 | 10.6 | 9.7 |
| 30 | 1 | H | H | CH₃ᵃ | H | H | H | 69.65 | 11.05 | 9.0 | 69.65 | 11.1 | 9.2 |
| 31 | 1 | H | H | H | C₂H₅ | H | H | 70.95 | 11.3 | 8.3 | 70.8 | 11.15 | 8.3 |
| 32 | 1 | H | H | H | n-C₇H₁₅ | H | H | 75.25 | 12.2 | 5.85 | 75.15 | 12.2 | 5.9 |
| 33 | 1 | H | H | H | n-C₁₁H₂₃ | H | H | 77.2 | 12.6 | 4.7 | 77.3 | 12.75 | 4.75 |
| 34 | 1 | n-C₇H₁₅ | H | H | H | H | H | 75.25 | 12.2 | 5.85 | 75.15 | 12.2 | 5.9 |
| 35 | 1 | n-C₁₁H₂₃ | H | H | H | H | H | 77.2 | 12.6 | 4.7 | 77.3 | 12.75 | 4.75 |

Note:
ᵃ5-methyl substituent.

EXAMPLES 36–39

Preparation of certain 3-(α-piperidyl)propan-1-ols (i) A solution of 1-alkene (0.2 mole) in chloroform (100 ml.) was added dropwise, over a 15 min. period, to be cooled (2°) solution of m-chloroperbenzoic acid (0.24 mole) in chloroform (400 ml.). The temperature of the reaction mixture was maintained below 10° by ice-cooling. The reaction was monitored by pipetting 1 ml. aliquots of the reaction mixture into water (25 ml.) and titrating against N/10 sodium thiosulphate using potassium iodide/starch indicator. The reaction mixture was stirred until the reaction was complete (about 100 mins.) and then the excess perbenzoic acid was destroyed by shaking the reaction mixture with a 10% aqueous solution of sodium sulphite. The sodium sulphite solution was removed and then the organic layer was extracted with aqueous sodium bicarbonate. The organic layer was then washed twice with water, dried over potassium carbonate and evaporated in vacuo to give an oil which was distilled under reduced pressure to afford a 1,2-epoxyalkane.

(ii) Phenyl lithium was prepared by the reaction of freshly cut lithium (0.3 mole) in sodium dried ether (225 ml) with freshly distilled bromobenzene (0.15 mole) under an atmosphere of nitrogen. To this solution was added dropwise 2-methylpyridine (0.15 mole) in sodium dried ether (30 ml.) and the resultant red/brown solution was stirred at room temperature for 1 h.

(iii) The ether solution of 2-picolyl lithium was cooled in ice and a solution of 1,2-epoxyalkane (0.15 mole) in sodium dried ether (30 ml.) was added slowly with stirring over a period of 1 h. After acidification with 50% hydrochloric acid, the aqueous layer was separated, basified with a saturated aqueous solution of sodium carbonate and extracted with ether. The ethereal layer was dried over sodium sulphate, evaporated in vacuo and distilled under reduced pressure to give a 2-(α-pyridyl)1-alkylpropanol.

(iv) A solution of the 2-(α-pyridyl)-1-alkylpropanol (0.1 mole) in absolute ethanol (250 ml.) was boiled under reflux whilst sodium metal (30 g.) was added portionwise over a period of approximately 0.75 h. The refluxing was continued for a further 2 h., and then the solution was allowed to cool to ambient temperature. The solution was carefully acidified (to pH 1) by the addition of, consecutively, dilute hydrochloride acid (20 ml.) and concentrated hydrochloric acid. The solution was basified with 30% aqueous sodium hydroxide and ether extracted. The combined ether extracts were dried over sodium sulphate, concentrated and the residue distilled in vacuo to give 3-(α-piperidyl)propan-1-ol. These compounds were used in the biocidal tests given later. Analytical results are given in Table V.

EXAMPLES 40 TO 51

Preparation of certain 3-alkylperhydropyrido(1,2-c)(1,3)Oxazepines

A 3-(α-piperidyl)propan-1-ol (0.08 mole, prepared as described above) was shaken with an excess of 40% aqueous alkyl aldehyde for 0.5 h. The mixture was basified with 50% aqueous sodium hydroxide and extracted with ether. The ethereal extracts were combined, dried over sodium sulphate, concentrated and the residual oil distilled in vacuo to give a 3-alkylperhydropyrido(1,2-c)(1,3)oxazepine. The compounds obtained were used in the biocidal tests given later. Analytical results are given in Table VI.

TABLE V

3-(piperidyl) propan-1-ols

| Compound No. | X | R¹ | R² | R³ | R⁵ | R⁶ | m. pt.*/b. pt.⁺ | Calculated (%) C | H | N | Found (%) C | H | N |
|---|---|---|---|---|---|---|---|---|---|---|---|---|---|
| 36 | 2 | H | H | C₂H₅ᵃ | H | H | — | | | | | | |
| 37 | 2 | CH₃ | H | H | H | H | — | 68.7 | 12.2 | 8.9 | 68.7 | 12.3 | 8.95 |
| 38 | 2 | C₂H₅ | H | H | H | H | 98–99°* | 70.1 | 12.4 | 8.2 | 70.15 | 12.4 | 8.3 |
| 39 | 2 | n-C₈H₁₇ | H | H | H | H | 166–167°⁺ at 0.13 mm Hg. | 75.2 | 13.0 | 5.5 | 75.3 | 13.0 | 5.7 |

ᵃ5-ethyl substituent

TABLE VI

| | | | | | Perhydropyrido (1,2-c) (1,3) Oxazepine | | | | Analysis | | | | | |
|---|---|---|---|---|---|---|---|---|---|---|---|---|---|---|
| | | | | | | | | | Calculated (%) | | | Found (%) | | |
| Compound No. | X | $R^1$ | $R^2$ | $R^3$ | $R^4$ | $R^5$ | $R^6$ | m. pt.*/b. pt+ | C | H | N | C | H | N |
| 40 | 2 | H | H | H | H | H | H | 90–91° at + 15 mm Hg | 69.6 | 11.0 | 9.0 | 69.5 | 10.85 | 9.1 |
| 41 | 2 | H | H | $C_2H_5$[a] | H | H | H | — | | | | | | |
| 42 | 2 | H | H | H | $CH_3$ | H | H | — | 71.0 | 11.3 | 8.3 | 71.0 | 11.4 | 8.5 |
| 43 | 2 | H | H | H | $C_2H_5$ | H | H | 64–70° at + 0.2 mm Hg | 72.1 | 11.55 | 7.6 | 72.0 | 11.5 | 7.5 |
| 44 | 2 | H | H | H | n-$C_7H_{15}$ | H | H | 115–117° at + 0.15 mm Hg | 75.8 | 12.3 | 5.5 | 75.95 | 12.4 | 5.55 |
| 45 | 2 | H | H | H | n-$C_{11}H_{23}$ | H | H | 129–132° at + 0.05 mm Hg | 77.6 | 12.7 | 4.5 | 77.4 | 12.8 | 4.65 |
| 46 | 2 | H | H | H | p-$NO_2C_6H_5$ | H | H | 75–78°* | 65.2 | 7.3 | 10.1 | 65.15 | 7.1 | 10.2 |
| 47 | 2 | $CH_3$ | H | H | H | H | H | 86–87° at + 5.0 mm Hg | 71.0 | 11.3 | 8.3 | 70.85 | 11.25 | 8.3 |
| 48 | 2 | $C_2H_5$ | H | H | H | H | H | 125–126° at + 12 mm Hg | 72.1 | 11.55 | 7.6 | 72.1 | 11.4 | 7.5 |
| 49 | 2 | n-$C_8H_{17}$ | H | H | H | H | H | 130–132° at + 8 mm Hg | 76.3 | 12.4 | 5.2 | 76.25 | 12.6 | 5.2 |
| 50 | 2 | H | H | $CH_3$[b] | H | H | H | — | | | | | | |
| 51 | 2 | H | H | $CH_3$[c] | H | H | H | — | | | | | | |

[a] 8-ethyl substituent
[b] 7-methyl substituent
[c] 6-methyl substituent

Trials for testing the barnicidal and algicidal activity of biocidal agents in accordance with the invention were conducted as follows:

1. Barnacle Toxicity Tests

The biocidal agents were screened for their toxicity towards early stage nauplii of *Elminius modestus* (Darwin) and *Balanus balanoides* (L), depending on the season. Duplicate batches of laboratory reared nauplii were exposed, for 24 hours, to 75 ml of test solutions maintained at 20° C., in the case of *E modestus*, or 10° C. in the case of *B balanoides*. The percentage kill was then recorded. To determine the relative activity of the biocidal agents they were initially tested at a concentration of $10^{-5}$ g ml$^{-1}$, and any showing 100% kill at this level were retested at a concentration of $10^{-6}$ g ml$^{-1}$.

Test concentrations of $10^{-5}$ g ml$^{-1}$ were prepared by dissolving 0.1 g of biocidal agent in 10 ml of analytical grade acetone, then taking 1 ml of this solution and diluting it to 1 liter with filtered, fresh sea water. Test concentrations of $10^{-6}$ g ml$^{-1}$ were prepared by dissolving 0.01 g of biocidal agent in 10 ml of analytical grade acetone, then taking 1 ml of this solution and diluting it to 1 liter with filtered, fresh sea water.

Substantially no barnicidal activity was exhibited by a 0.1% solution of analytical grade acetone in sea water towards control nauplii.

The results are shown in Table VII from which it can be seen that α-n-dodecyl-2-piperidylcarbinol (compound No. 8) and 1-n-octanyl, 1-n-decyl and 1-n-dodecylperhydrooxazolo[3,4-a]pyridine (compounds Nos. 18,21 and 23 respectively), and 1-n-octyl-3-(α-piperidyl)propan-1-ol (compound No. 39) were the most effective biocidal agents towards early stage barnacle nauplii. The toxicity of all five compounds was comparable to that of an equivalent concentration of cupric ions. Other biocidal agents according to this invention also exhibited some barnicidal activity against *E modestus* (Darwin) and *B balanoides* (L), but their toxicity was generally less than that of cupric ions.

2. Algal Toxicity Tests

The test method was a spectrophotometric measurement of the optical density of chlorophyll b in a suspension of *Chlamydomonas reinhardii* which had been exposed to a $10^{-5}$ g ml$^{-1}$ concentration of the biocidal agent under test for 24 hours. The performance of each agent as an algicidide was evaluated against a non-toxic control and various concentrations of mercuric chloride.

a. A solution of each biocidal agent was prepared by dissolving a 0.01 g sample in 10 ml of analytical grade ethanol. 1.0 ml of this solution was then diluted to 50 ml with Erdschreiber medium. Finally, 8 ml of this solution was added to an equal volume of *C reinhardii* solution contained in a plastic vial. The final concentration of agent in solution was $10^{-5}$ g ml$^{-1}$.

b. A range of control solutions containing mercuric ions was prepared by dissolving 0.135 g mercuric chloride in 500 ml Erdschreiber medium to afford a solution in which the concentration of mercuric chloride was approximately $1 \times 10^{-3}$ mole liter$^{-1}$. By the addition of appropriate amounts of this solution to Erdschreiber medium, three further solutions containing, respectively, $10^{-4}$, $10^{-5}$, and $10^{-6}$ mole liter$^{-1}$ of mercuric chloride were obtained. 8 ml of each of the above solution was then taken and added separately to an equal volume of *C reinhardii* solution. The concentrations of mercuric chloride in the four final solutions were $5 \times 10^{-4}$, $5 \times 10^{-5}$, $5 \times 10^{-6}$, and $5 \times 10^{-7}$ mole liter$^{-1}$.

c. Four non-toxic controls were prepared by adding 8 ml of the *C reinhardii* culture to an equal volume of Erdschreiber medium. Readings were taken for two of these control solutions at the beginning of the test.

d. Duplicate batches of the test, mercuric reference and control solutions were shaken under ambient temperature and light conditions for 24 hours. The optical density at 676 nm was then read on a Pye Unicam SP 1800 spectrophotometer, using a silica cell of 1 cm path length.

Results are shown in Table VIII from which it can be seen that α-n-octanyl-2-piperidylcarbinol (compound No. 3), α-n-decyl-2-piperidylcarbinol (compound No. 6) and 1-n-decylperhydro-oxazolo[3,4-a]pyridine (compound No. 21) and 3-octylperhydropyrido[1,2-c][1,3]oxazepine (compound No. 49) were particularly effective against *C reinhardii*, in fact more effective than an equivalent concentration of mercuric chloride. Further, it can also be seen from Table VIII that other biocidal agents according to this invention exhibited algicidal activity against *C reinhardii* which was substantially equal to that shown by an equivalent concentration of mercuric chloride, whilst others exhibited some algicidal activity but less than an equivalent concentration of mercuric chloride.

Typical anti-fouling compositions in accordance with this invention will now be described by way of example. Further trials on the drying properties of these compositions are also given by way of example.

A sample of 1-n-decylperhydro oxazolo[3,4-a]pyridine (compound No. 21) was prepared for anti-fouling paint trials and the compatibility of this compound with various media was evaluated for 3 ratios of anti-fouling agent to total medium solids.

The composition of the media solutions which were tested for compatibility with the toxicant are given in Table IX.

Mixtures, comprising one of the compositions shown in Table IX and either 0%, 25%, 33% or 50% (by weight of solids) of the anti-fouling agent were prepared. Those mixtures which were compatible were brushed onto glass panels and left to dry at room temperature. The extent of drying of the paint films was assessed after 2, 4, 6 and 24 hours and the drying times of mixtures containing toxicant were compared with the toxicant-free composition.

In all but one case the toxicant-composition mixtures were compatible for up to 50% (by weight of solids) of toxicant. In all cases addition of the toxicant increased the drying time of the mixture in comparison with the toxicant-free composition. However, in most tests, the addition of up to 33% of toxicant led to only a slight increase. The results are given in Table X.

TABLE VII

Toxicity of biocidal agents towards early stage barnacle nauplii

| | % Kill Concentration of biocidal agent | |
|---|---|---|
| Compound No | $10^{-5}$ g ml$^{-1}$ | $10^{-6}$ g ml$^{-1}$ |
| 1 | 100 | 0 |
| 3 | 100 | 37.5 |
| 6 | 100 | 92.5 |
| 8 | 100 | 100 |
| 9 | 0 | — |
| 12 | 0 | 0 |
| 14 | 0 | 0 |
| 15 | 0 | 0 |
| 18 | 100 | 100 |
| 21 | 100 | 100 |
| 23 | 100 | 100 |
| 24 | 0 | 0 |
| 32 | 0 | 0 |
| 33 | 100 | 0 |
| 39 | 100 | 100 |
| 46 | 100 | 0 |
| 49 | 100 | 75 |
| 50 | 100 | 97.5 |

TABLE VIII

Toxicity of biocidal agents at a concentration of $10^{-5}$ g ml$^{-1}$ towards *Chlamydomonas Reinhardii*

| | | Conc$^n$ of mercuric chloride (mole liter$^{-1}$) that exhibits equivalent toxicity | | |
|---|---|---|---|---|
| Compound No | Conc$^n$ (mole liter$^{-1}$) | $5 \times 10^{-4}$ to $5 \times 10^{-5}$ | $5 \times 10^{-5}$ to $5 \times 10^{-6}$ | $5 \times 10^{-6}$ to $5 \times 10^{-7}$ |
| 1 | $7.00 \times 10^{-5}$ | — | — | ✓ |
| 3 | $4.41 \times 10^{-5}$ | ✓ | — | — |
| 6 | $3.92 \times 10^{-5}$ | ✓ | — | — |
| 8 | $3.53 \times 10^{-5}$ | — | ✓ | — |
| 9 | $2.95 \times 10^{-5}$ | — | ✓ | — |
| 12 | $6.45 \times 10^{-5}$ | — | — | ✓ |
| 14 | $4.44 \times 10^{-5}$ | — | — | ✓ |
| 15 | $3.56 \times 10^{-5}$ | — | ✓ | — |
| 18 | $4.18 \times 10^{-5}$ | — | ✓ | — |
| 21 | $3.75 \times 10^{-5}$ | ✓ | — | — |
| 23 | $3.39 \times 10^{-5}$ | — | ✓ | — |
| 24 | $2.85 \times 10^{-5}$ | — | ✓ | — |
| 32 | $4.18 \times 10^{-5}$ | — | — | ✓ |
| 33 | $3.39 \times 10^{-5}$ | — | ✓ | — |
| 36 | $5.80 \times 10^{-5}$ | ✓ | — | — |
| 37 | $6.40 \times 10^{-5}$ | — | — | ✓ |
| 38 | $5.84 \times 10^{-5}$ | — | — | ✓ |
| 40 | $6.50 \times 10^{-5}$ | — | ✓ | — |
| 41 | $5.50 \times 10^{-5}$ | ✓ | — | — |
| 43 | $5.50 \times 10^{-5}$ | — | — | ✓ |
| 44 | $3.95 \times 10^{-5}$ | — | — | ✓ |
| 45 | $3.23 \times 10^{-5}$ | — | — | ✓ |
| 46 | $3.60 \times 10^{-5}$ | — | ✓ | — |
| 47 | $5.90 \times 10^{-5}$ | — | — | ✓ |
| 48 | $5.50 \times 10^{-5}$ | — | — | ✓ |
| 49 | $3.70 \times 10^{-5}$ | ✓ | — | — |
| 50 | $5.90 \times 10^{-5}$ | — | — | ✓ |

Note:
✓ indicates the range of concentration of mercuric chloride that exhibits the same degree of toxicity as the listed biocidal agent.

TABLE IX

Compositions tested for compatibility with 1-n-decylperhydro oxazolo [3,4-a] pyridine (Compound No 21)

A. Epoxy resin solids (Epikote 1001*) (70 g), Secondary Butanol (15 g), Curing Agent (Versamid 115*) (70 g) 2-Ethoxyethanol (Oxitol*) (15 g), Naphtha (30 g)
B. Epoxy resin solids (Epikote 1001*) (70 g), Secondary Butanol (15 g), Curing agent (Versamid 115*) (70 g), 2-Ethoxyethanol (Oxitol*) (15 g), Resin solids (WW*) (140 g), Naphtha (90 g)
C. Cyclised rubber (Plastoprene No 2*) (60 g), Naphtha (40 g)
D. Cyclised rubber (Plastoprene No 2*) (60 g), Resin solids (WW*) (70 g), Naphtha (70 g)
E. Chlorinated rubber (Alloprene*) (60 g), Naphtha (40 g)
F. Chlorinated rubber (Alloprene*) (60 g), Resin solids (WW*) (70 g), Naphtha (70 g)
G. Castor oil modifier (Plastokyd E-D4*) (60 g), Epoxide resin ester (Shellsol*) (40 g), Drying agent (Nuosyn driers*) (0.5 g)
H. Castor oil modifier (Plastokyd E-D4*) (60 g), Epoxide resin ester (Shellsol*) (40 g), Drying agent (Nuosyn driers*) (0.5 g), Resin solids (WW*) (70 g), Naphtha (30 g)

NOTE:
*signifies a Trade Mark

TABLE X

Compatibility and drying characteristics of media with 1-n-decylperhydro-oxazolo [3,4-a] pyridine (toxicant)

| Composition | Max compatible (%)$^a$ | Effect on drying time$^b$ | |
|---|---|---|---|
| | | up to 33%$^c$ | at 50%$^d$ |
| A | 50$^e$ | Slightly increased | Slightly increased |
| B | 50$^e$ | Increased | Did not dry |
| C | 50 | Slightly increased | Did not dry |
| D | 50 | Slightly increased | Did not dry |
| E | 25 | Slightly increased | — |
| F | 50 | Slightly increased | Did not dry |
| G | 50 | Did not dry | Did not dry |

TABLE X-continued

Compatibility and drying characteristics of media with 1-n-decylperhydro-oxazolo [3,4-a] pyridine (toxicant)

| Composition | Max compatible (%)[a] | Effect on drying time[b] | |
|---|---|---|---|
| | | up to 33%[c] | at 50%[d] |
| H | 50 | Slightly increased | Did not dry |

NOTE:
[a]The maximum amount (by % of dry weight) of toxicant that was compatible with a given composition;
[b]The drying time of mixtures of toxicant and composition was compared with that of the pure composition. The paint surface was assessed after 2, 4, 6 and 24 hr;
[c]Effect on drying time for mixtures containing up to 33% of toxicant;
[d]Effect on drying time for mixtures containing 50% of toxicant;
[e]50% mixture was slightly cloudy, 25 and 33% mixtures were clear.

Trials for testing the anti-fungal activity of biocidal agents in accordance with the invention were conducted as follows:

A two phase system comprising equal volumes of DIESO fuel and an aqueous solution of nutrients was employed in tests to screen the potential antifungal agents against *Cladosporium resinae*.

a. Preparation of Spore Suspension

*Cladosporium resinae* was cultured on malt extract agar slopes and incubated at 25° C. When heavy fungal growth had been obtained the slopes were kept at 5° C. until required. The spore suspensions were prepared in 10 ml of sterile quarter strength Ringers solution and 0.1% tween 80, giving approximately $5 \times 10^5$ spores $ml^{-1}$.

b. Preparation of Aqueous Solution of Nutrients

The aqueous solution of nutrients used in the two phase system contained the following:

| | |
|---|---|
| FeCl$_3$ solution (15 g in 25 ml of water) | 0.01 ml |
| MgSO$_4$ 7H$_2$O | 0.02 g |
| CaCl$_2$ 2H$_2$O | 0.0026 g |
| KH$_2$PO$_4$ | 0.1 g |
| K$_2$HPO$_4$ | 0.1 g |
| NH$_4$NO$_3$ | 0.1 g |
| Distilled water | 1000 ml |

Aliquots of 2.5 ml of this solution were placed in test tubes and autoclaved for 15 min at 15 psi.

c. Preparation of Solutions of Potential Fungicides in Fuel

A solution of each potential antifungal compound was prepared in Naval 20 pour (47/50) DIESO which had been filtered using Whatman No 42 filter papers. For the initial screening tests concentrations of 625 and 125 ppm of biocidal agent in DIESO fuel were used. The solutions of biocidal agent in DIESO fuel were prepared by first dissolving the agent in either dimethyl formamide (DMF) or acetone and then adding this homogeneous mixture to DIESO fuel. The concentration of biocidal agent in the initial solution with DMF or acetone was arranged such that, when the concentration of biocidal agent in the subsequent solution with DIESO fuel was 625 ppm the concentration of DMF or acetone in the DIESO fuel was 1% by volume. It was shown that a 1% solution of DMF or acetone in DIESO fuel did not inhibit the growth of *C resinae*.

d. Experimental Procedure

Using a pasteur pipette one drop of spore suspension was placed on top of 2.5 ml of the aqueous solution of nutrients contained in a test-tube. 2.5 ml of DIESO fuel containing a known concentration of the potential antifungal agent was then poured on to the aqueous solution. (In the two phase system obtained the less dense DIESO fuel was the upper layer). The two phase system was then incubated at 25° C. and, during the next 20 days, examined visually for fungal growth at the fuel-water interface.

e. Assessment of fungal growth

The amount of growth of *C resinae* at the fuel-water interface within systems containing a known concentration of biocidal agent was compared with the amount of growth at the interface of a non-toxic control (ie DIESO fuel containing 1% DMF or acetone over an equal volume of an aqueous solution of nutrients).

The amount of fungal growth was then assessed as follows:

0 = no growth
− = less growth than the non-toxic control
+ = equal or greater growth than the non-toxic control Results are given in Table XI

TABLE XI

Toxicity of biocidal agents towards *Cladosporium resinae*

| | 10 days[a] | | 20 days[a] | |
|---|---|---|---|---|
| Compound No | 625 ppm[b] | 125 ppm[b] | 625 ppm[b] | 125 ppm[b] |
| 2 | 0 | 0/— | — | + |
| 3 | 0 | 0 | 0 | 0 |
| 4 | 0 | 0 | 0 | 0 |
| 6 | 0 | 0 | 0 | 0 |
| 8 | 0 | 0 | 0 | 0 |
| 10 | 0 | 0 | 0 | — |
| 11 | 0 | — | 0 | — |
| 12 | 0 | 0 | 0 | — |
| 13 | 0 | — | 0 | — |
| 14 | — | — | — | 0/— |
| 15 | — | 0/— | — | — |
| 16 | 0 | 0 | — | — |
| 17 | — | — | — | 0/— |
| 18 | 0 | 0 | 0 | |
| 19 | 0 | 0 | 0 | 0 |
| 21 | 0 | 0 | 0 | — |
| 24 | 0 | 0 | 0 | — |
| 25 | 0 | 0 | 0 | — |
| 26 | 0 | 0 | 0 | 0 |
| 27 | 0 | 0 | 0 | 0 |
| 29 | 0 | 0 | 0 | — |
| 30 | 0 | — | — | — |
| 31 | 0 | 0 | 0 | — |
| 32 | — | — | — | 0/— |
| 33 | 0 | — | — | 0/— |
| 34 | 0 | — | — | — |
| 35 | 0 | — | 0 | — |
| 24c | 0 | 0 | — | — |
| 36 | 0 | 0 | 0 | — |
| 37 | 0 | 0 | 0 | — |
| 41 | 0 | — | 0 | 0/— |
| 44 | 0 | — | — | — |
| 45 | 0 | — | 0 | — |
| 46 | 0 | 0 | 0 | — |
| 47 | 0 | 0 | 0 | — |

Note:
[a]time allowed for fungal growth at interface;
[b]concentration of biocidal agent in fuel.

Compounds 3, 6 and 8 were then screened by similar experiments for their toxicity against *Cladosporium resinae* at lower concentrations (100, 10 and 1 ppm) of biocidal agent in DIESO fuel. Results are given in Table XII

TABLE XII

Toxicity of selected biocidal agents towards *Cladosporium resinae*

| Compound No | 6 days | | | 12 days | | |
|---|---|---|---|---|---|---|
| | 100 ppm | 10 ppm | 1 ppm | 100 ppm | 10 ppm | 1 ppm |
| 3 | 0 | + | + | + | + | + |
| 6 | 0 | + | + | 0 | + | + |

TABLE XII-continued

Toxicity of selected biocidal agents towards *Cladosporium resinae*

| Compound No | 6 days | | | 12 days | | |
|---|---|---|---|---|---|---|
| | 100 ppm | 10 ppm | 1 ppm | 100 ppm | 10 ppm | 1 ppm |
| 8 | 0 | + | + | 0 | + | + |

Further biocidal compounds according to this invention were screened for antifungal activity by the slide germination technique of R. N. Smith and B. Crook as described in the 4th International Biodetermination Symposium, BAB, Berlin, 1978. Results, given in terms of percentage germination after 48 hours, are listed in Table XIII.

TABLE XIII

Toxicity of selected biocidal agents, in % germination, in the slide germination test

| | % Germination | | |
|---|---|---|---|
| Compound No. | 100 ppm | 10 ppm | 1 ppm |
| 36 | 0 | 83 | 100 |
| 37 | 0 | 24 | 100 |
| 38 | 0 | 49 | 100 |
| 41 | 0 | 11 | 100 |
| 43 | 0 | 90 | 100 |
| 44 | 0 | 49 | 100 |
| 45 | 0 | 48 | 100 |
| 46 | 78 | | |
| 47 | 0 | 86 | 100 |
| 48 | 0 | 19 | 70 |
| 49 | 0 | | |
| 51 | 0 | | |

We claim:

1. A composition for inhibiting algal, barnacle and fungal growth in aquatic environments consisting essentially of a biocidally effective amount of an active component which is a synthetic heterocyclic compound of the structure:

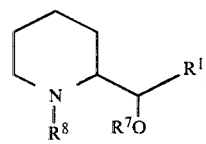

wherein
$R^1$ is an alkyl radical containing 8, 10 or 12 carbon atoms and
$R^7$ and $R^8$, when taken separately, are hydrogen atoms or, when taken together, are $-CH_2-$, in conjunction with an acceptable diluent or carrier.

2. A composition according to claim 1 wherein $R^7$ and $R^8$ are taken together and are $-CH_2-$.

3. A composition according to claim 1 wherein $R^1$ is $n-C_8H_{17}$.

4. A composition according to claim 3 wherein $R^7$ and $R^8$ are taken together and are $-CH_2-$.

5. A method of inhibiting algal, barnacle and fungal growth in aquatic environments consisting essentially of applying a biocidally effective amount of a composition according to claim 1 to an aquatic environment, or to a surface within an aquatic environment, to prevent algal, barnacle or fungal growth.

* * * * *